United States Patent
Forge et al.

(10) Patent No.: US 9,724,423 B2
(45) Date of Patent: Aug. 8, 2017

(54) THIXOTROPIC α-LACTALBUMIN HYDROGELS, METHOD FOR PREPARING SAME AND USES THEREOF

(75) Inventors: Vincent Forge, Vourey (FR); Carole Mathevon, Sassenage (FR); Frédéric Pignon, Grenoble (FR)

(73) Assignees: Commissariat a l'Energie Atomique et aux Energies Alternatives, Paris (FR); Centre National de la Recherche Scientifique, Paris (FR)

( * ) Notice: Subject to any disclaimer, the term of this patent is extended or adjusted under 35 U.S.C. 154(b) by 214 days.

(21) Appl. No.: 14/110,577

(22) PCT Filed: Apr. 10, 2012

(86) PCT No.: PCT/FR2012/000138
§ 371 (c)(1),
(2), (4) Date: Feb. 18, 2014

(87) PCT Pub. No.: WO2012/136909
PCT Pub. Date: Oct. 11, 2012

(65) Prior Publication Data
US 2014/0221289 A1     Aug. 7, 2014

(30) Foreign Application Priority Data
Apr. 8, 2011  (FR) .................................. 11 53077

(51) Int. Cl.

| | | |
|---|---|---|
| A61K 38/00 | (2006.01) | |
| C07K 9/00 | (2006.01) | |
| A61K 47/42 | (2017.01) | |
| A23J 3/08 | (2006.01) | |
| A61K 38/38 | (2006.01) | |
| C07K 14/76 | (2006.01) | |
| C09D 5/04 | (2006.01) | |
| A61K 8/64 | (2006.01) | |
| A61Q 17/00 | (2006.01) | |
| A61K 8/04 | (2006.01) | |
| A61K 38/18 | (2006.01) | |
| A61L 26/00 | (2006.01) | |
| A61Q 19/00 | (2006.01) | |
| A23L 29/281 | (2016.01) | |

(52) U.S. Cl.
CPC ................. *A61K 47/42* (2013.01); *A23J 3/08* (2013.01); *A23L 29/281* (2016.08); *A23L 29/284* (2016.08); *A61K 8/042* (2013.01); *A61K 8/64* (2013.01); *A61K 38/1808* (2013.01); *A61K 38/38* (2013.01); *A61L 26/008* (2013.01); *A61Q 17/005* (2013.01); *A61Q 19/00* (2013.01); *A61Q 19/007* (2013.01); *C07K 14/76* (2013.01); *C09D 5/04* (2013.01); *A23V 2002/00* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 6,139,900 A | | 10/2000 | Foegeding et al. |
| 2010/0034881 A1 | * | 2/2010 | Schneider et al. ............ 424/484 |

FOREIGN PATENT DOCUMENTS

| | | | |
|---|---|---|---|
| EP | 0459566 A1 | * | 5/1991 |
| EP | 0 459 566 | | 12/1991 |
| WO | 2008/130252 | | 10/2008 |
| WO | 2010/099185 | | 9/2010 |

OTHER PUBLICATIONS

Graveland-Bikker et. al. (Trends in Food Science & Technology 17 (2006) 196-203.*
Merriam-Webster, paint definition, http://www.merriam-webster.com/dictionary/paint. last visited May 28, 2015.*
Blanchet et al., Repliement des Proteines et Formation de Fibres Amyloides. Le cas de l'Alhpa-Lactalbumine, Retrieved from http://tel.archives-ouvertes.fr/docs/00/32/76/86/PDF/These_finale.pdf, pp. 1-263, 2008.
Goers et al., Conformational Prerequisites for Alpha-Lactalbumin Fibrillation, Biochemistry, 41, pp. 12546-12551, 2002.
Graveland-Bikker et al., Unique Milk Protein Based Nanotubes: Food and Nanotechnology Meet, Trends in Food Science & Technology, 17, pp. 196-203, 2006.
Bolder, Fibril Assemblies in Aqueous Whey Protein Mixtures, Journal of Agricultural and Food Chemistry, 54, pp. 4229-4234, 2006.
Database WPI, Thomson Scientific, AN 2010-Q12928, Nov. 10, 2010.

* cited by examiner

*Primary Examiner* — Jeanette Lieb
(74) *Attorney, Agent, or Firm* — Morgan, Lewis & Bockius LLP (57) ABSTRACT

The present invention relates to shear-thinning α-lactalbumin hydrogels, which have a threshold and are thixotropic, to a method for preparing same and to the use thereof.

16 Claims, 7 Drawing Sheets

THIXOTROPIC α-LACTALBUMIN HYDROGELS, METHOD FOR PREPARING SAME AND USES THEREOF

The present invention relates to the preparation of hydrogels which have advantageous properties, using a by-product of the milk industry: α-lactalbumin, to the resulting hydrogels and to the use thereof, in particular for preparing biomaterials.

The hydrogels produced in the context of the present invention have particular rheological characteristics which make them advantageous for certain applications; in fact, they are thixotropic gels capable, under a sufficient stress, of becoming destructured until they are in a liquid state and then of becoming restructured once left to stand.

The protein used to produce the hydrogels is α-lactalbumin (subsequently denoted α-La), in particular α-La of bovine origin. This milk protein is found more particularly in whey. It therefore has the advantage of being a natural protein which is available in large amounts in the cheese industry, since cheese is produced from the milk "curds" (caseins which have been precipitated and from which the whey has been removed).

A gel is composed of a molecule which, in the presence of an appropriate solvent, self-assembles via chemical or physical interactions, and becomes organized as a network. The specific processes which result in the formation of gels depend on the physicochemical properties and on the interactions of the components of the gel. When the solvent is water, the term hydrogel is used.

A hydrogel is a network of polymer chains initially soluble in water, but having become insoluble after crosslinking. Hydrogels are superabsorbent natural or synthetic polymers (they can contain more than 99% of water). They also have a degree of flexibility that is very similar to that of natural tissues, because of their high water content. Their physical characteristics, their permeability and also their biocompatibility make them excellent candidates as biomaterials used for medical applications including molecule delivery and also tissue engineering. Depending on the nature of the transverse bonds, hydrogels are separated into two categories: chemical gels resulting from conventional methods of crosslinking with covalent bonds and physical gels which result from the self-assembly of macromolecules (for example, carbohydrate or protein macromolecules) and constitute networks held together by molecular entanglements and/or weak bonds (hydrophobic bonds, ionic bonds, hydrogen bridges and van der Waals forces); the molecular interactions of these physical gels can be disrupted by environmental changes such as temperature, pH, ionic strength, light or even a given biological molecule. The gelling is therefore reversible in response to one or more of these stimuli.

The preparation of hydrogels from milk proteins is already known. Milk proteins are natural vehicles for bioactive molecules by virtue of their structural and physicochemical properties such as their ability to bind ions and small molecules or else their self-assembling and gelling properties. Despite the amount of materials based on milk proteins (caseins or whey proteins) already used in various industries, many studies on these proteins are continuing and are aimed at developing novel innovative nano-objects: such as edible and biodegradable food films made from milk proteins combined with other natural biopolymers (Chen 1995; Le Tien, Vachon et al. 2001); coacervates or nanovesicles of caseins or of other milk proteins which have in particular been developed as delivery systems (Audic, Chaufer et al. 2003; Semo, Kesselman et al. 2007; Livney 2010); or else milk protein gels.

Among the milk protein gels, mention may first of all be made of the gelling of caseins, which can be obtained under various conditions: through acidity at pH 4.6; through the action of rennet, the active ingredient of which is chymosin, an enzyme which performs a proteolytic cleavage leading to the aggregation of micelles, and which is used for the encapsulation of probiotic bacteria (Heidebach, Forst et al. 2009a); through the action of transglutaminase, an enzyme which bridges together certain amino acids (essentially glutamic acid and lysine) contributing to the polymerization of proteins, and which is also used for the microencapsulation of probiotic cells (Heidebach, Forst et al. 2009b); through the action of genipin, a natural protein-crosslinking agent, for the controlled delivery of molecules in the intestines (contraction of the hydrogel at acid pH (stomach) and then swelling at neutral pH and therefore release of the active ingredient (intestine)) (Song, Zhang et al. 2009).

It is also known practice to induce gelling of whey proteins by increasing the temperature (Paulsson, Hegg et al. 1986). Like other hydrogels, the gels made from whey proteins exhibit a swelling behavior which is pH-sensitive and usable for the targeted delivery of molecules (Gunasekaran, Ko et al. 2007). β-Lactoglobulin gels, which are also temperature-induced, are very widely studied and have been characterized using various techniques such as TEM (transmission electron microscopy), WAXS (wide angle X-ray scattering) and FTIR (Fourier transform infrared spectroscopy) (Kavanagh, Clark et al. 2000). The denaturation of proteins can lead to hydrophobic interactions between them, especially β-lactoglobulin (b-Lg) and bovine serum albumin (BSA) which posses free thiols and can therefore interchange disulfide bridges: for example, BSA nanospheres have been produced with a magnetic particle and/or a photosensitizer and are usable in cancer treatments (Rodrigues, Simioni et al. 2009). A cold gelling process has recently been developed and makes the resulting gels potentially advantageous for molecule delivery. The advantage of these gels lies in the fact that heat-sensitive bioactive agents can be added after the heat treatment of the wheys but before the gelling which is subsequently induced by adding salts (preferably calcium salts) or by reducing the pH.

Many rheometric measurements have been carried out on β-lactoglobulin gels alone (Gosal, Clark et al. 2004b) or as a mixture with α-lactalbumin (Kavanagh, Clark et al. 2000). They have made it possible to determine the factors, pH and ionic strength, affecting the physical characteristics of gels (Loveday, Rao et al. 2009). β-Lactoglobulin (b-Lg) gels induced by prolonged exposure to high temperatures (80° C.) form in two steps and appear to be essentially composed of polypeptides of partially degraded β-lactoglobulin (Akkermans, Venema et al. 2008; Oboroceanu, Wang et al. 2010). b-Lg gels can also be obtained by dissolving the protein in a particular water/alcohol mixture. The rheological and structural characteristics of these gels are different (Gosal, Clark et al. 2004a; Gosal, Clark et al. 2004c; Loveday, Rao et al. 2009).

Other types of known gels made from whey proteins are formed from α-lactalbumin nanotubes (Ipsen, Otte et al. 2001). These nanotubes form by self-assembly of α-lactalbumin fragments under certain conditions (minimum protein concentration and protein/calcium ratio) (Graveland-Bikker, Ipsen et al. 2004; Ipsen and Otte 2007). The particularity of these fibers is that they are obtained only in the presence of calcium and with a protein which has previously undergone controlled proteolysis by a particular serine protease, extracted from *Bacillus licheniformis* (Ipsen and Otte 2007).

The formation of gels from intact α-lactalbumin, induced by high temperatures (80° C.), has been shown at neutral pH in two articles studying in particular the influence of α-lactalbumin on the gelling of β-lactoglobulin (Hines and Foegeding 1993; Kavanagh, Clark et al. 2000). More particularly, the team of Kavanagh et al., have monitored the gelling at 80° C. of various concentration ratios between b-Lg and α-La and also of the proteins alone constituting their controls. The control corresponding to α-La alone has, at pH 7, a gelling time which is 10 times slower than that observed with b-Lg alone. These α-La gels have not attracted the attention of researchers and have not therefore been characterized from a structural and rheological point of view. An α-La gel prepared according to the conditions described by Kavanagh et al. has been prepared by the applicant (see example 3); it exhibits macroscopic characteristics that are different than those of the hydrogels developed by the applicant; it is hard, elastic and irreversible (it does not change shape when it is subjected to a stress).

Finally, the thesis by C. Blanchet ("Repliement des protéines et formation de fibres amyloïdes. Le cas de l'α-lactalbumine" ["Protein folding and formation of amyloid fibers. The case of α-lactalbumin"], defended on Jun. 23, 2008) describes a process for preparing a suspension of α-lactalbumin at 40° C., at pH 2, at various salt concentrations (NaCl from 0 to 150 mM); however, these processes are not carried out with the specific purpose of preparing gels, but to characterize the behavior of the α-lactalbumin.

The gels obtained with 150 mM of NaCl were, however, characterized: they have a shear-thinning behavior; it is not suggested in this thesis that such gels described can exhibit thixotropic behavior and such behavior cannot be deduced from the tests presented in this thesis.

The applicant has reproduced the process for preparing an α-lactalbumin hydrogel as described in this thesis and has been able to confirm experimentally that the resulting gels are not thixotropic (see example 4 hereinafter).

A shear-thinning (or pseudoplastic) fluid is a fluid of which the viscosity decreases if the shear stress or the strain rate which is applied thereto increases (see preamble of example 2).

It should be specified that shear-thinning fluids are not necessarily thixotropic, this is the case, for example, for carbopol gels (Piau 2007; Tokpavi, Jay et al. 2009).

In the context of these studies, the applicant has managed to develop shear-thinning α-lactalbumin hydrogels which have a yield point and are thixotropic.

Figure 1:
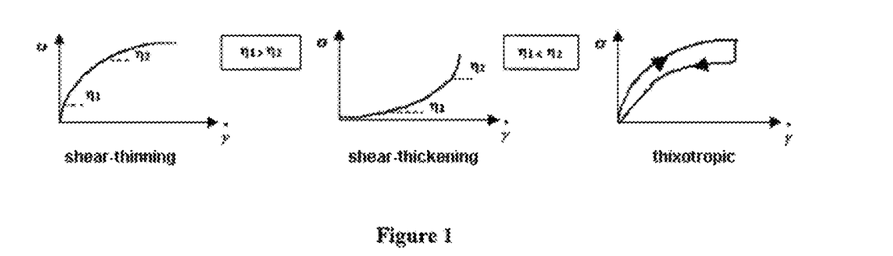
FIG. 1 illustrates the behavior of the thixotropic fluids of which the viscosity decreases over time when a constant shear rate is applied thereto, and which, reversibly, increases again if the shear is interrupted.

The commonly accepted definition of thixotropy (Mewis 1979; Pignon, Magnin et al. 1998) is the following: a material is commonly referred to as thixotropic if, starting from a resting state for a sufficiently long period of time, its viscosity decreases with time and its structure modifies, when a constant shear rate is applied thereto. In a reversible manner, if the shear is interrupted, the viscosity increases again, and the material then gradually recovers the consistency and the structure that it had at rest (FIG. 1).

This characteristic is highly sought after, in particular for spreading and applying numerous products in foods (milk or soy protein gels, WO 2008/130252), in paints or in cosmetic products. It may also be very useful as a noninvasive method of in situ injection of hydrogels in the targeted delivery of molecules or for tissue reconstruction. An article published in Nature Nanotechnology shows that thixotropic gels composed, for example, of PEG-silica can be used and have various advantages in 3D cell culture (Pek, Wan et al. 2008).

The hydrogels according to the invention are said to have a yield point since a minimum stress must be applied to allow the material to flow beyond a strain, denoted critical strain $\gamma_c$, having, in the context of the present invention, a value greater than 0.1, preferably between 0.1 and 1. The critical strain is achieved when a sufficiently high stress (yield stress) is applied to a hydrogel completely at rest so that said hydrogel begins to flow; it is identified graphically by the crossing of the curve of the storage modulus G' and of that of the loss modulus G" (see example 2 and FIG. 6).

More particularly, the present invention relates to a process for preparing an α-lactalbumin hydrogel from an aqueous suspension of α-lactalbumin at a concentration $C_{a-La}$ of between 5 and 60 mg/ml, comprising the following steps:
  a) suspending the α-lactalbumin in an acidic aqueous solution having an ionic strength of less than or equal to 60 mM, preferably less than 50 mM, and more preferentially having a value of 30 mM; said suspending consisting in:
    (a1) preparing an acidic aqueous solution having a concentration of protons expressed in mM determined by the sum: (numerical value of $C_{a-La}$ expressed in g/l)+10;
    (a2) suspending the α-lactalbumin in said acidic aqueous solution; and
    (a3) if necessary, adjusting the pH to a value of between 1.5 and 2.5, preferably between 1.8 and 2.2, the pH more preferentially being 2.0;
  b) forming the gel from said α-lactalbumin suspension obtained at the end of step a); said forming of the gel is carried out under the following conditions:
    at a temperature below 60° C., preferably between 35 and 55° C.;
    with stirring having a strength defined by a Reynolds number of between 37 and 1000, preferably between 300 and 500;
    for 10 hours to 1 week (168 hours), in particular between 48 and 96 hours, and
    in the absence of evaporation of water from said α-lactalbumin suspension.

The aqueous α-lactalbumin suspension may also be denoted solution in the subsequent text.

Surprisingly, despite a low or zero ionic strength of the aqueous solution used to prepare the a-La hydrogel, the applicant has noted that it is nevertheless possible to obtain a thixotropic hydrogel and that this hydrogel exhibits satisfactory stability over time; indeed, the applicant has observed that the hydrogels at low ionic strength are more stable over time than those obtained at high ionic strength (>60 mM), which become viscous over time. In addition, the preparation of hydrogel having a very low salt content is advantageous, for example, for uses as a food texturing agent.

α-Lactalbumin is a small globular metalloprotein of 14 kDa which has 4 disulfide bridges, it is structurally homologous to lysozyme and requires the presence of calcium for a functional structure. It is the most abundant protein in human whey and the second most abundant protein, after b-Lg, in bovine whey. It is one of the model proteins in folding studies since it is capable, under precise conditions, of adopting a particular partially folded state: the molten globule (MG) state (Permyakov and Berliner 2000).

a-La is the least allergenic milk protein (Restani, Ballabio et al. 2009) and despite a certain resistance to digestive enzymes in the presence of the other milk proteins, the peptides released by the action of various proteases on a-La are widely studied.

Many processes for enriching whey in a-La or for purifying a-La are used on an industrial scale: membrane filtration; column chromatography (IEX, SEC, HIC); enzymatic hydrolysis to degrade caseins or b-Lg, combined with membrane filtration or else isoelectric precipitation combined with heat treatment to precipitate a-La (Kamau, Cheison et al. 2010).

The process according to the invention can be carried out with any α-lactalbumin; according to one particular embodiment, this involves α-lactalbumin resulting from the cheese industry, originating from cow's, ewe's, goat's, buffalo's, camel's, mare's, etc., milk.

In the context of the implementation of the process according to the invention, the source of α-lactalbumin used preferably has a purity of at least 85%, preferentially of at least 90%. It is also possible to implement the process according to the invention with whey enriched in α-lactalbumin and having an α-lactalbumin content of at least 45% by weight.

Preferably, the α-lactalbumin suspension obtained at the end of step a) is filtered. This filtration can be carried out with a filter having a cutoff threshold such that it allows through objects having a molecular weight of less than or equal to 20 kDa, such as the a-La proteins, but retains microorganisms and other contaminants; use may thus be made of filters with a cutoff threshold of less than or equal to 0.5 μm, for example commercial 0.22 μm filters.

The implementation of step b) of forming the gel is carried out with a homogeneous temperature of the entire α-lactalbumin suspension.

The stirring of the α-lactalbumin suspension carried out during this step b) must also be homogeneous throughout the stirring vessel.

In order to characterize the strength of the stirring, which must be weak but not zero, independently of the geometry and of the size of the vessel and of the stirrer, the applicant has determined a Reynolds number value range suitable for carrying out the process according to the invention; thus, the Reynolds number must be between 37 and 1000, preferably between 300 and 500. The modes for determining the Reynolds number are detailed in example 1 hereinafter.

By way of example, when the process is carried out on a laboratory scale (α-lactalbumin suspension volume of between 1 ml and 100 ml), the stirring can be carried out using a turntable or else with a magnetic bar, the length of which is between 70% and 90% of the diameter of said vessel; in this case, the stirring speed is between 10 and 300 revolutions per minute (rpm).

The a-La gels are formed at acidic pH, favorable to the MG form and therefore to the fibrillation of the protein. The pH value is extremely important for the gel formation since it is, for example, impossible at pH 3 (Kavanagh, Clark et al. 2000).

During the implementation of step (a1) of the process according to the invention, the content of proteins making it possible to obtain the acidic pH required for the formation of the hydrogel can be obtained with a strong acid, for example HCl.

It is essential to carry out the acidification according to step (a1) before step (a2) of suspending the a-La.

The ionic strength used for the preparation of the hydrogel according to the invention and which is between 0 and 60 mM is obtained by the optional addition of salt which can be chosen from alkali or alkaline-earth metal halides, such as, for example, NaCl, KCl, $MgCl_2$, $CaCl_2$, etc.; alkali or alkaline-earth metal carbonates or a mixture thereof; phosphates, such as, for example, sodium phosphate or potassium phosphate, or else sulfates, such as, for example, sodium sulfate or magnesium sulfate, etc.

The salt concentration of the aqueous a-La solution is conventionally determined by those skilled in the art according to the desired ionic strength.

According to one particular variant of implementation of the process according to the invention, it is implemented without the addition of salt.

Example 2 which follows shows the rheological characterization of the a-La hydrogels obtained by means of the process according to the invention.

The present invention also relates to the α-lactalbumin hydrogels that can be obtained according to the process of the invention.

They are more specifically hydrogels having an α-lactalbumin content of between 5 and 60 mg/ml; a pH of between 1.5 and 2.5, preferably between 1.8 and 2.2, the pH more preferentially being 2.0; an ionic strength of less than or equal to 60 mM, preferably less than or equal to 50 mM, and even more preferentially having a value of 30 mM.

These hydrogels are characterized by having the behavior of a shear-thinning fluid which has a yield point (flow occurs when a critical strain of between 0.1 and 1 is applied) and is thixotropic; the viscosity of these hydrogels decreases if the shear stress or the strain rate which is applied thereto increases; in addition, these hydrogels become destructured under the influence of the shear (liquefaction) and become restructured when the shear ceases (solidification).

Produced from natural sources such as milk or whey, the α-lactalbumin hydrogels according to the invention fall within the context of sustainable development. The product is natural and therefore biodegradable, biocompatible, non-toxic and considered to be GRAS (generally recognized as safe). Furthermore, the production process is compatible with green chemistry processes, i.e. mild chemistry which preserves the environment since it uses neither solvent nor crosslinking agent.

Whey proteins, and in particular α-lactalbumin, have remarkable properties:
- their physicochemical properties are well known: structure, stability, solubility, affinity for metals, hydrophobicity, etc.;
- the self-assembly of the proteins occurs in the form of fibers, one of the foundations of nanotechnologies;
- they have high nutritional values;
- they exhibit various biological effects, observed especially using the peptides derived from the proteolysis thereof (Madureira, Pereira et al. 2007).

In addition, the use of these proteins on the industrial scale is suitable since:
- their source, whey, is inexpensive;
- the processes for purifying whey proteins on the industrial scale are already known;
- the amounts available are considerable: firstly, owing to the amount of α-La contained in whey (more than 1 g/l in bovine whey) and, secondly, owing to the amounts of whey available since it is a by-product of the cheese industry and therefore a material to be exploited.

Whey is the main waste from cheesemakers and casein producers. The main proteins in whey are β-lactoglobulin (b-Lg), α-lactalbumin (a-La), immunoglobulins, bovine serum albumin (BSA) and lactoferrin (Lf).

The amounts of whey available throughout the world are considerable. In France, 15 billion liters of whey are generated each year by the production of cow's cheeses. In the absence of a recovery solution, the whey not self-consumed by the livestock is dumped into rivers or spread in fields, with harmful consequences for the natural environment: pollution of water courses, lakes and groundwater and odor pollution. This pollution is mainly due to fermentation of the organic matter of whey (lactose and nitrogenous matter) and to the decrease in dissolved oxygen content of the water below an acceptable threshold. Indeed, the chemical oxygen demand and biological oxygen demand (COD and BOD) of this waste are high (COD of 50 to 70 g/l) and make it a seriously polluting material. The setting up of economically acceptable devices aimed at collecting and recovering the whey is today obligatory in order to reduce this environmental damage.

The high nutritional, functional and biological value of a-La justifies its interest in the food, pharmaceutical and cosmetic fields. The use of the a-La hydrogels according to the invention can be envisioned in the form of hydrogels as such, of course, but also in the form of films by spin-coating and then drying of the gels, or else in the form of threads by extrusion or electrospinning of the gels.

The applicant has demonstrated that the a-La hydrogels having an α-lactalbumin content of between 5 and 60 mg/l and prepared at acidic pH, i.e. between 1.5 and 2.5, preferably between 1.8 and 2.2 and more preferentially at pH 2.0, whatever their ionic strength, are shear-thinning, have a yield point and are thixotropic.

Although these hydrogels have an acidic pH at the end of their preparation, it is possible to increase their pH in order to adapt it to the uses to which it is desired to put said hydrogels while at the same time preserving their rheological properties.

Thus, according to another of its subjects, the present invention relates to thixotropic hydrogels having an α-lactalbumin content of between 5 and 60 mg/ml and prepared at an acidic pH, but the pH of which it has been possible to subsequently increase, for a use where their rheological properties prove to be advantageous.

Composed of edible products, the a-La hydrogels find in particular numerous applications in the field of the food-processing industry.

Thus, the present invention relates to a food product comprising a thixotropic α-lactalbumin hydrogel having an α-lactalbumin content of between 5 and 60 mg/ml and to the use of such an α-lactalbumin hydrogel as a food texturing agent. According to one particular embodiment, the ionic strength of said gels is between 0 and 60 mM, preferably less than 50 mM, and more preferentially has a value of 30 mM.

Depending on the desired consistency of the food product, it may contain between 0.5% and 98% of thixotropic α-lactalbumin hydrogel by weight relative to the total weight of said food product.

By virtue of the α-lactalbumin properties summarized above, the hydrogels according to the invention are particularly suitable for the preparation of biomaterials. The term "biomaterials" is intended to mean materials intended to be in temporary or permanent contact with various tissues, organs or fluids of a living being, for diagnostic, preventive or therapeutic purposes; biomaterials also comprise materials intended to be implanted in a living organism.

Thus, the present invention also relates to the thixotropic α-lactalbumin hydrogels having an α-lactalbumin content of between 5 and 60 mg/ml, for use as a product used for the treatment and/or healing of wounds; in particular, these hydrogels have an ionic strength of between 0 and 60 mM. Indeed, the α-lactalbumin hydrogels meet the criteria generally considered for the preparation of a dressing: biocompatibility and absence of cytotoxicity; prevention of dehydration of the wound with maintenance of a moist environment; protection against dust and bacteria; maintenance of gas exchanges; easy application to the wound and easy removal after healing.

In addition, in order to improve their effectiveness, the hydrogels may also comprise one or more active compounds, such as compounds capable of promoting healing of the skin, for example by promoting epithelialization by delivering specific active molecules (for example: EGF) or antimicrobial compounds.

Thus, the present invention relates to a dressing composed of at least one thixotropic α-lactalbumin hydrogel having an α-lactalbumin content of between 5 and 60 mg/ml; according to one particular variant, these hydrogels have an ionic strength of between 0 and 60 mM, preferably less than 50 mM, and more preferentially having a value of 30 mM. Optionally, said dressing also comprises at least one active compound, such as a healing agent or an antimicrobial agent.

According to one variant, the dressing according to the invention comprises an external film that is permeable to air and impermeable to liquids and to microorganisms; such a film can, for example, be composed of polyurethane.

According to another of its subjects, the present invention relates to a cosmetic composition comprising at least one thixotropic α-lactalbumin hydrogel having an α-lactalbumin content of between 5 and 60 mg/ml, and to the use of at least one such thixotropic α-lactalbumin hydrogel for preparing a cosmetic composition, in particular, as a skin moisturizing agent in compositions intended for skincare (gel, cream, lotion, etc.) or as a surfactant (washing products, shampoo, etc.); according to one particular variant, these hydrogels have an ionic strength of between 0 and 60 mM, preferably less than 50 mM, and more preferentially having a value of 30 mM.

Finally, by virtue of their thixotropic behavior, the hydrogels having an α-lactalbumin content of between 5 and 60 mg/ml are advantageously used for preparing paints, in particular industrial paints. Indeed, the hydrogels enable these paints to remain solid during their transport and storage, thus avoiding undesirable running, while at the same time being easy to spread upon use. In addition, the hydrogels make it possible to improve the stability and preservation of industrial paints which are normally used in continually stirred tanks. Through stirring carried out only at the time they are used, they make it possible in addition to make an energy saving.

Thus, the present invention further relates to the use of a thixotropic α-lactalbumin hydrogel having an α-lactalbumin content of between 5 and 60 mg/ml, for preparing paints, in particular industrial paints, and to paints comprising such a hydrogel; according to one particular variant, these hydrogels have an ionic strength of between 0 and 60 mM, preferably less than 50 mM, and more preferentially having a value of 30 mM.

In addition to the above arrangements, the invention also comprises other arrangements which will emerge from the description which follows, which refers to exemplary embodiments of the present invention, and also to the appended figures in which.

FIGURES

EXAMPLE 1

Determination of the Reynolds Number Value Range for the Stirring Strength for Implementing the Process According to the Invention The Reynolds number represents the stirring strength; in a stirred reactor, it is equal to $$Re = \frac{\rho V d}{\mu}$$

where:
$\rho$ is the density of the fluid mixed, in Kg·m$^{-3}$,
V is the rotational velocity of the magnetic bar (in m/s),
$\mu$ is the viscosity of the fluid mixed (in Pa·s), and
d is the size of the stirring tool (for example, the length for the case of a magnetic bar) (in m).

The rotational velocity N of the magnetic bar is defined by the velocity applied by the stirrer, for a velocity range of from 0 to 300 rpm.

The relationship between the velocity V in m/s and the rotational velocity N in rpm is the following:

$$V = \frac{\pi d}{30} N$$

That is to say, it is possible to evaluate a Reynolds number:

$$Re = \frac{\rho \pi d^2}{30 \mu} N.$$

The fluids mixed (alpha-lactalbumin powder+aqueous suspension) have a viscosity very close to that of water because the concentration of alpha-lactalbumin powder is sufficiently low to not greatly modify the viscosity of the suspension when it is introduced into the water: consequently, during the initial mixing of the suspension, the viscosity and the density of the suspension stirred will be taken to be equal to that of water, i.e.: $\rho=1000$ K/$\mu^3$, $\mu=10^{-3}$ Pa·s.

The size of the magnetic bar used is d=6×10$^{-3}$ m in length.

The table below groups together examples of Reynolds number values suitable for the mixture recommended for obtaining thixotropic gels from suspensions of alpha-lactalbumin:

| N (rpm) | V (m/s) = $(2 \times 10^{-4} \pi) \times N$ | Re = $1.2 \pi N$ |
|---|---|---|
| 10 | $2\pi \times 10^{-3}$ | $12\pi = 37.699$ |
| 100 | $2\pi \times 10^{-2}$ | $120\pi = 376.99$ |
| 300 | $2\pi \times 0.03$ | $360\pi = 1130.973$ |

$$Re = \frac{1000, \pi, (6 \cdot 10^{-3})^2}{30 \cdot 10^{-3}} N = 1.2 \, \pi N$$

EXAMPLE 2

Preparation of α-Lactalbumin Hydrogels According to the Invention 2.1. Hydrogel Prepared from Purified a-La The purified protein "α-lactalbumin from bovine milk Type III, calcium depleted, 85%" which is sold under catalog reference L6010 by Sigma and is lyophilized is resuspended in an aqueous solution of HCl optionally containing NaCl.

The HCl concentration depends on the final concentration of a-La. It is calculated in mM by adding 10 to the numerical value of the desired concentration of a-La.

For example, if it is desired to have 40 mg/ml of a-La, the HCl concentration for resuspending it will be 40+10=50 mM.

First of all, it is necessary to prepare the HCl solution at the predetermined concentration and then to add thereto NaCl at between 0 and 60 mM. Next, it is necessary to weigh out the required amount of a-La. This amount depends on the final concentration of protein and on the volume of gel to be prepared. The a-La concentrations used range from 5 to 60 mg/ml.

The protein is dissolved in the defined volume of HCl solution and then the pH is adjusted to 2.0±0.1 with a few microliters of 1M HCl. The solution is subjected to magnetic stirring using a magnetic bar and incubated overnight at a temperature which can range from 37 to 45° C. The following day, i.e. approximately 16 h later, the gel is formed.

2.2. Hydrogel Prepared from Whey with a 45% Enrichment in a-La

The preceding protocol is reproduced using a lactoserum with a 45% by weight enrichment in a-La, supplied by the company Armor Protéines.

EXAMPLE 3

Determination of the Viscoelastic Characteristics of the a-La Hydrogels by Rheology Notions of Rheology Rheology is a branch of physics which studies the flow or the strain of bodies under the effect of the stresses which are applied thereto, taking into account the rate of application of these stresses or more generally their variation over time.

At a high concentration of α-lactalbumin, the formation of amyloid fibers is accompanied by an increase in viscosity of the solution. When the fibers are formed, they interact with one another to form a gel. This increase in viscosity is monitored by rheometry. The sample placed in a rheometer will be subjected to a certain stress ($\tau$) which is dependent on the shear rate ($\dot{\gamma}$) applied. The stress $\tau$ varies with the shear rate $\dot{\gamma}$ and the ratio between the two makes it possible to determine the viscosity ($\eta$) of the fluid studied. When $\tau$ is proportional to $\dot{\gamma}$, then $\eta$ is a constant and the fluid is Newtonian, whereas if $\tau$ is not proportional to) $\dot{\gamma}$, then the fluid is non-Newtonian and may be of various natures:

if the viscosity $\eta$ decreases when $\tau$ and $\dot{\gamma}$ increase, then the fluid is a shear-thinning fluid;

conversely, if $\eta$ increases when $\tau$ and $\dot{\gamma}$ increase, then the fluid is a shear-thickening fluid.

Thixotropic fluids are shear-thinning, their viscosity decreases under the same stress over time because of a destructuring of the material. These fluids are reversible since, when the stress is stopped, the material becomes restructured and regains its initial viscoelastic characteristics.

The viscoelastic characteristics of a material are obtained by determining the dynamic viscosity moduli according to Hooke's law: $\tau = G\dot{\gamma}$ where G has two components, G' and G", which serve to quantify the viscous or elastic behavior of materials. G' is the storage (elastic) modulus and G" is the loss (viscous) modulus. When the elastic nature dominates, G'>>G" and, conversely, when the viscous nature dominates, G'<<G".

Rheometric Behavior of the Gels 3.1. Rheometric Measurements

The characterization of the behavior under shear flow of the a-La gels was carried out by rotary rheometry. The measurements were carried out using an applied-torque rotary rheometer (ARG2, TA Instruments, 78 Guyancourt, France). The geometries used are titanium cone-plate geometries (angle 4°, diameter 20 mm, truncation 113 µm). In order to avoid evaporation of the sample during the measurements, the atmosphere was saturated with water around the sample. For the measurements in harmonic shear, a preliminary study made it possible to define the levels of strain and of optimum frequency for which the measurements are part of the linear regime range. In this range, the applied harmonic shear stress does not modify the rheological behavior of the suspensions, and merely probes the viscoelastic moduli of the gels without disrupting them. The frequency of 0.1 Hz was defined as being part of the linear regime regardless of the applied strain and the restructuring time of the samples. All the measurements in harmonic shear will therefore be carried out at this frequency of 0.1 Hz. In the monitoring of the restructuring, a strain $\gamma$ of 0.01 was also defined as not disrupting the measurement G' and G", and will be systematically used for monitoring the restructuring of the samples.

3.2. Temporal Monitoring of Destructuring-Restructuring of the Gels Under Shear 3.2.1. Small Strain Behavior A procedure for monitoring consistency by harmonic shear was set up and used systematically for various samples under given concentration and ionic strength conditions.

Figure 2:
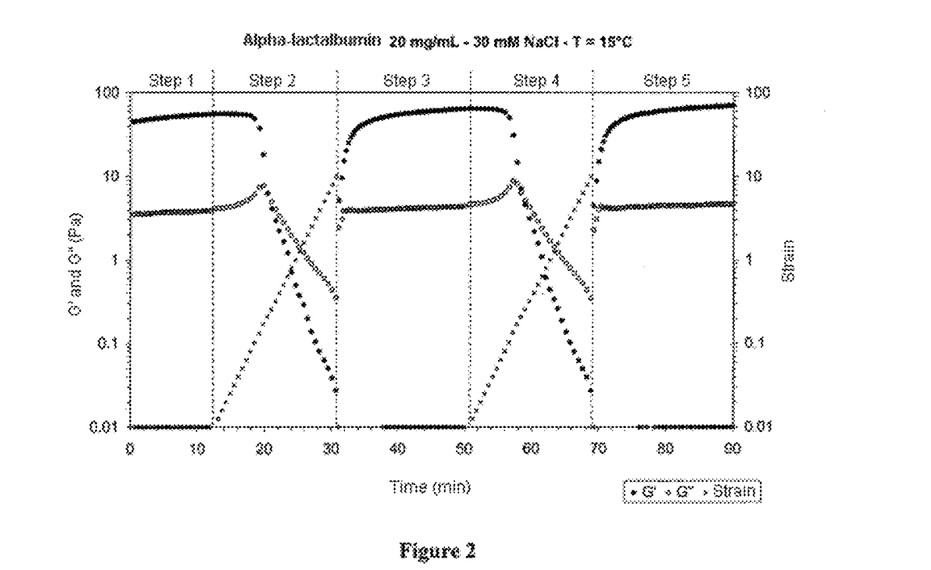
FIG. 2 represents the monitoring of the destructuring and of the restructuring at 15° C. over time of a hydrogel of a-La at 20 mg/ml and 30 mM of NaCl in small strains in harmonic shear. Various procedures for monitoring the change in the elastic modulus G' (solid circle) and viscous modulus G" (open circle) as a function of time and of the applied strain (crosses), were applied; the stresses applied at each step are detailed in example 2 which follows.

FIG. 2 shows a succession of harmonic shears for an a-La gel (20 mg/ml a-La-30 mM NaCl) according to the strain amplitude conditions recorded in table I below:

TABLE I

Strain conditions applied during the procedure
for harmonic shear destructuring-restructuring of the
a-La gels

| Step | $\dot{\gamma}$ |
|---|---|
| 1- Temporal monitoring of the restructuring following placement of the gel in the gap in the tools. | 0.01 |
| 2- Strain ramp for destructuring the gel | 0.01 to 10 |
| 3- Temporal monitoring of the restructuring | 0.01 |
| 4- Strain ramp for destructuring the gel | 0.01 to 10 |
| 5- Temporal monitoring of the restructuring | 0.01 |

During steps 1, 3 and 5 at constant strain amplitude, the recovery in consistency of the gel corresponding to its restructuring can be demonstrated.

During steps 2 and 4, the gradual increase in the strain amplitude makes it possible to monitor the destructuring of the gel brought about by the preceding shear. At increasing strain amplitude, the elastic modulus G' and viscous modulus G" decrease regularly until a critical strain $\gamma_c$ beyond which the levels drop greatly, which demonstrates the destructuring of the gel and the change from an elastic behavior to a viscous behavior (G' becomes less than G").

The recovery in consistency at the beginning of steps 3 and 5, characterized by the increase in G' and G" over time, clearly demonstrates the thixotropic behavior of the gel. During the restructuring, it can be noted that there is a short time Tr1 of restructuring with a strong recovery in consistency which is about 300 s, followed by a longer time Tr2 during which the increases in G' and G" follow slower kinetics.

Figure 12:
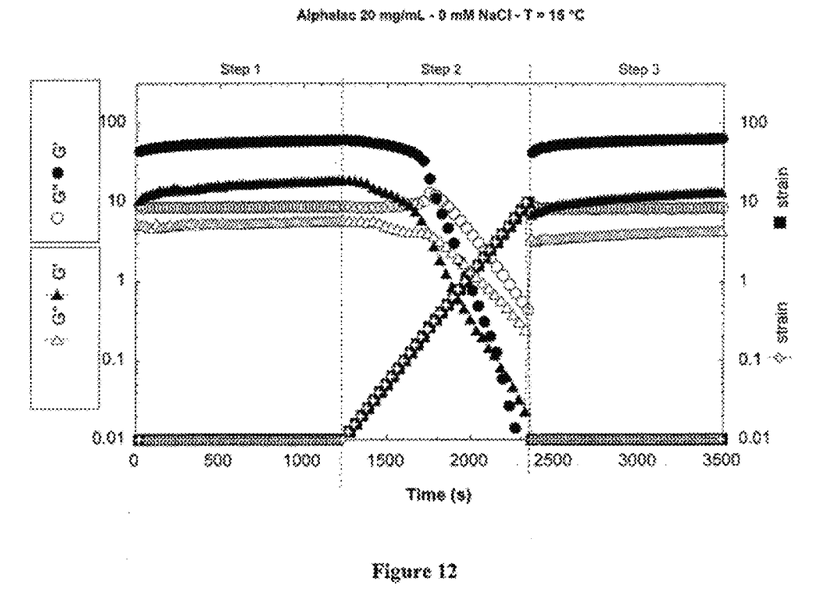
FIG. 12 represents the monitoring of the destructuring and of the restructuring at 15° C. over time of two hydrogels of a-La at 20 mg/ml and 0 mM of NaCl (one prepared from purified a-La, the second from whey with a 45% enrichment in a-La) in small strains in harmonic shear. Various procedures for monitoring the change in the elastic moduli G' (solid circle for the hydrogel prepared from purified a-La; solid triangle for the hydrogel prepared from whey with a 45% enrichment in a-La) and viscous moduli G" (open circle for the hydrogel prepared from purified α-La; open triangle for the hydrogel prepared from whey with a 45% enrichment in a-La) as a function of time and of the applied strain (crosses), were applied; the stresses applied during steps 1 to 3 are detailed in example 2 which follows.

The same observations can be made when applying the first three steps described above to the hydrogel prepared from whey with a 45% by weight enrichment in a-La; the gel obtained is therefore itself also thixotropic.

3.2.2. Large Strain Behavior

In order to demonstrate the thixotropic behavior on strains of larger amplitudes, a large strain simple shear was applied, followed by a small strain harmonic shear in order to monitor the recovery in consistency of the gel over time. In order to demonstrate the effect of the shear rate on the level of destructuring reached and also on the restructuring kinetics, various large strain shear rates were applied.

TABLE II

Strain conditions applied during the
procedures for large strain destructuring and for
monitoring restructuring of the a-La gels in harmonic
shear

| Steps | $\dot{\gamma}$ |
|---|---|
| 6 - Temporal monitoring of the restructuring following large strain destructuring at 10 s$^{-1}$ | 0.01 |
| 7 - Strain ramp for destructuring the gel | 0.01 to 10 |
| 8 - Temporal monitoring of the restructuring | 0.01 |

Figure 3:
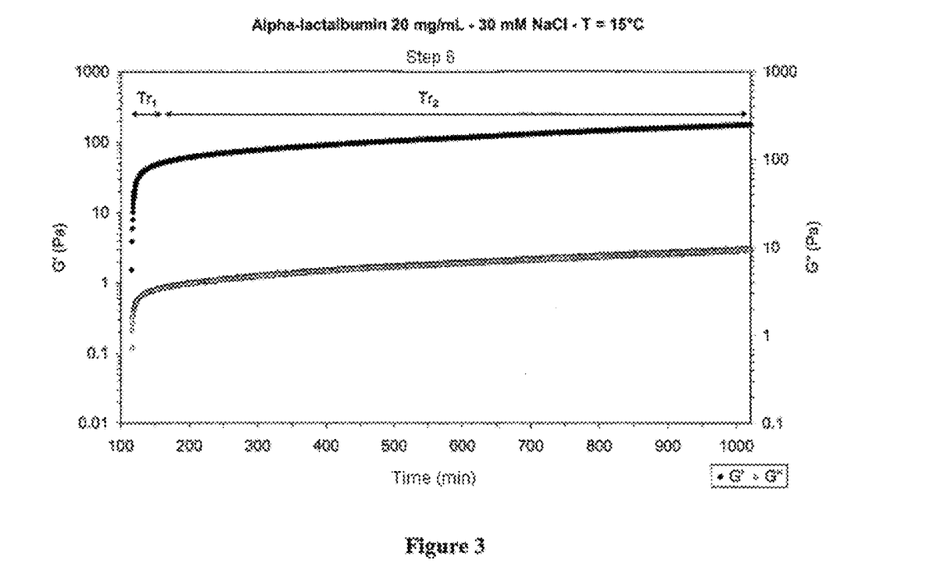
FIG. 3 represents the monitoring of the restructuring at 15° C. over time of a hydrogel of a-La at 20 mg/ml and 30 mM of NaCl after large strain destructuring at a shear rate of 10 s$^{-1}$; the elastic modulus G' is represented as solid circles and the viscous modulus G" as open circles.

Represented in FIG. 3 is the recovery in consistency (step 6) after a large strain shear at a shear rate of 10 s$^{-1}$ for 300 s. It can again be noted that there is a first period Tr1 over which the elastic and viscous moduli cross strongly with time, and a second period Tr2 for which restructuring kinetics are much slower.

Figure 4:
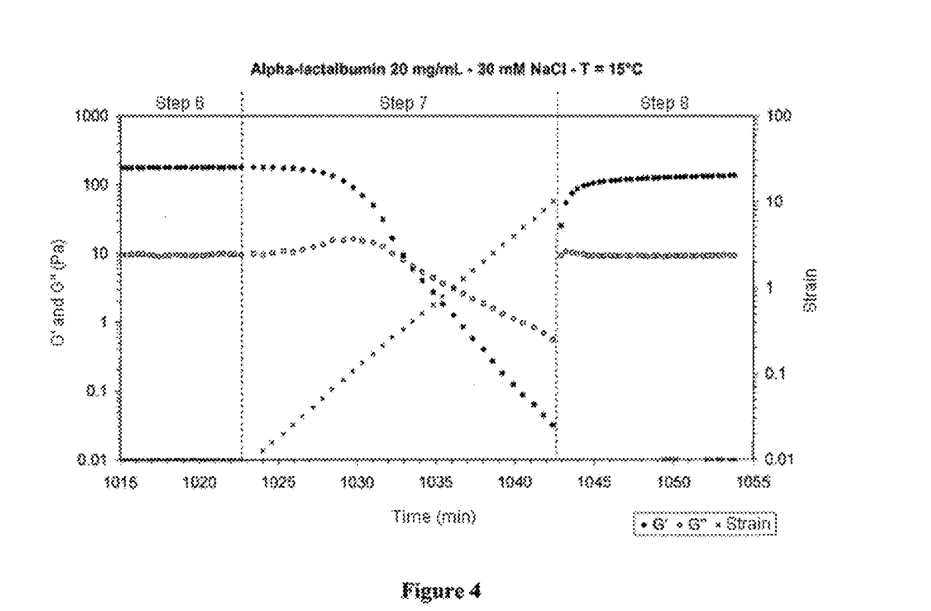
FIG. 4 illustrates the end of the monitoring of the restructuring at 15° C. over time of a hydrogel of α-La at 20 mg/ml and 30 mM of NaCl after large strain destructuring at a shear rate of 10 s$^{-1}$ (step 6), then step 7 of harmonic shear destructuring at increasing strain amplitude, and finally step 8 of monitoring the small strain recovery in consistency.

Following lengthy monitoring of restructuring over 1000 min (more than 16 h), a procedure for destructuring in harmonic shear at increasing strain amplitude is again applied (step 7) (see FIG. 4), followed by a recovery in consistency at small strain (step 8) (see FIG. 4).

Figure 5:
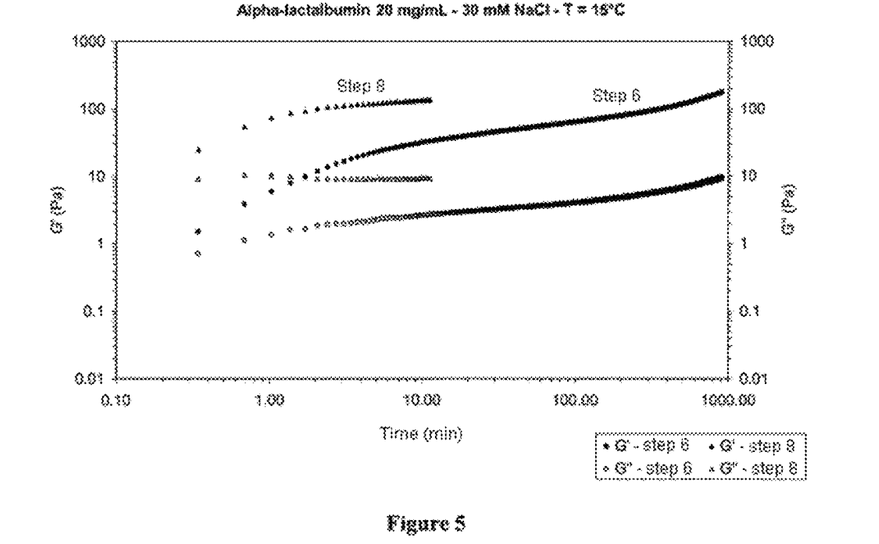
FIG. 5 is a comparison of the kinetics of restructuring at 15° C. over time of a hydrogel of a-La at 20 mg/ml and 30 mM of NaCl (step 6) after large strain destructuring at a shear rate of 10 s$^{-1}$ (G' is represented as solid triangles and G" as open triangles) and (step 8) after destructuring in small strains in harmonic shear at increasing strain amplitude (G' is represented as solid circles and G" as open circles).

FIG. 5 shows a comparison of the two recoveries in consistency either after a large strain simple shear (step 6), or after a harmonic shear at increasing strain amplitude (step 8). The results demonstrate different restructuring kinetics according to these two destructuring modes employed. The increasing strain kinetics following a large strain simple shear are much slower than during increasing-amplitude small strain harmonic shear. Indeed, the large strain shear manages to destructure the sample at a higher level than that obtained during a small strain shear. This result again demonstrates the importance of the type of stress and of its strength on the level of destructuring reached in the sample during shearing thereof, which is an indication of the behavior of thixotropic systems.

Figure 6:
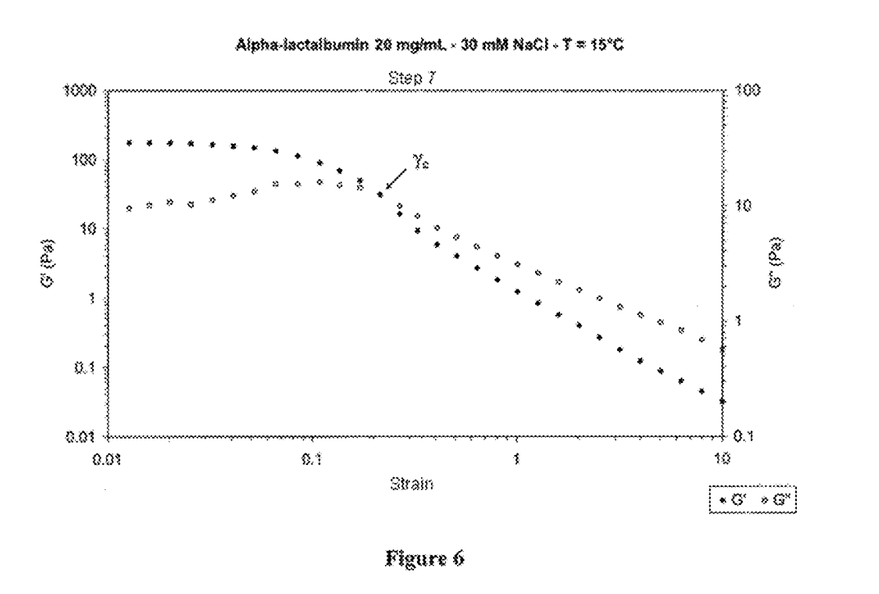
FIG. 6 represents the monitoring of the destructuring in harmonic shear at increasing strain amplitude at 15° C. over time of a hydrogel of a-La at 20 mg/ml and 30 mM of NaCl: identification of the critical strain $\gamma_c$ of approximately 0.2 beyond which the sol-gel transition begins to appear (step 7).

Represented in FIG. 6 is the change in the viscoelastic moduli as a function of strain, measured during a procedure for destructuring (step 7) in harmonic shear at increasing strain amplitude. It is demonstrated that the critical strain $\gamma_c$ beyond which the gel begins to flow, identified by the crossing of G' and G", is about 0.2.

3.3. Effect of Ionic Strength on the Thixotropic Behavior of the a-La Gels

Figure 7:
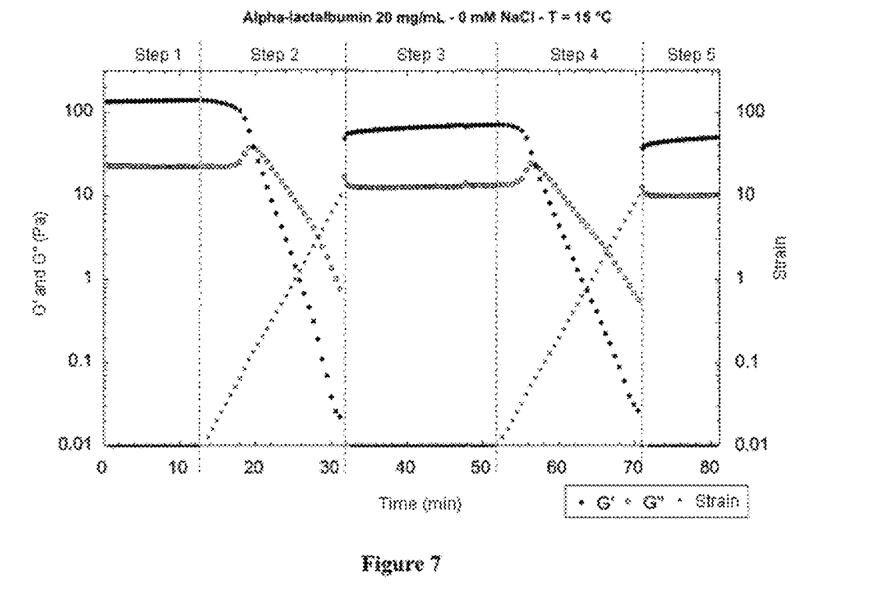
FIG. 7 represents the monitoring of the destructuring and of the restructuring at 15° C. over time of a hydrogel of a-La in small strains in harmonic shear; 20 mg/ml-0 mM NaCl.
Figure 8:
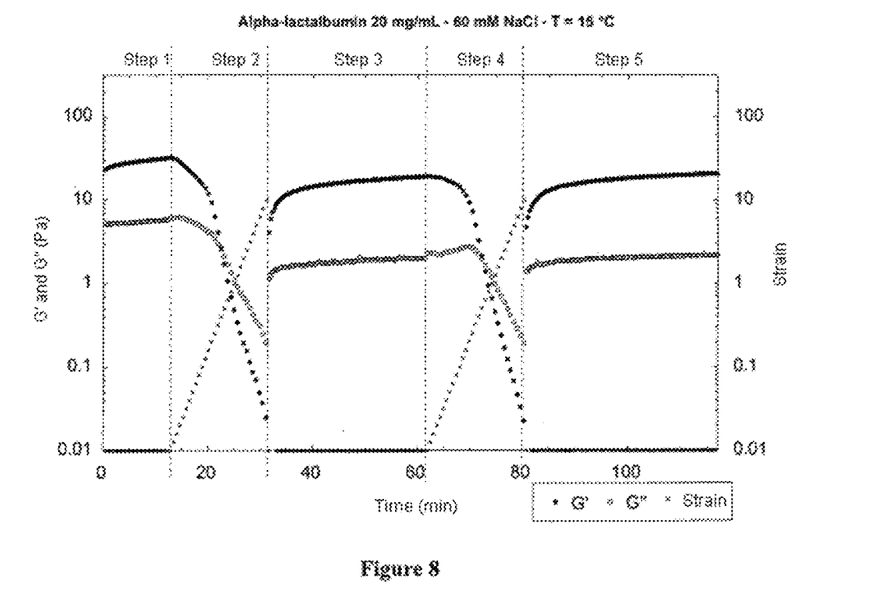
FIG. 8 represents the monitoring of the destructuring and of the restructuring at 15° C. over time of a hydrogel of a-La in small strains in harmonic shear; 20 mg/ml-60 mM NaCl.
Figure 9:
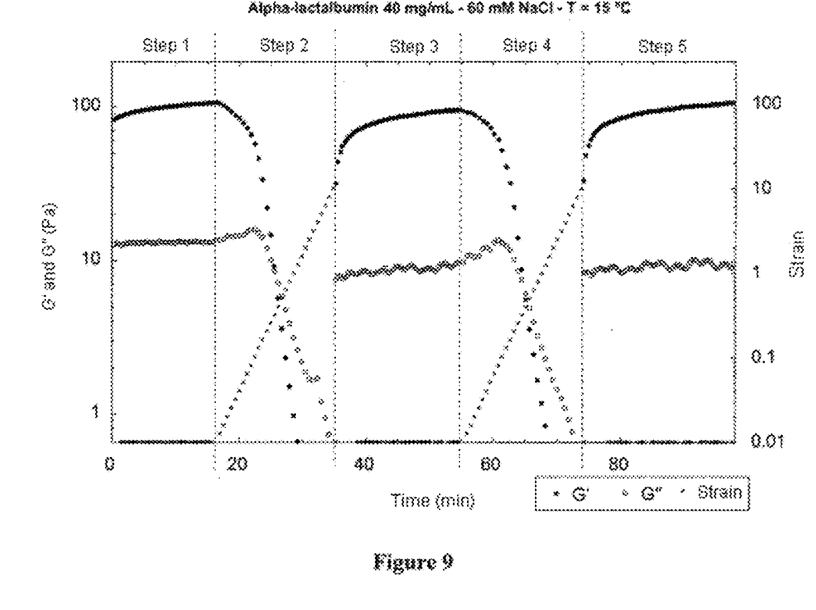
FIG. 9 represents the monitoring of the destructuring and of the restructuring at 15° C. over time of a hydrogel of a-La in small strains in harmonic shear; 40 mg/ml-60 mM NaCl.

In order to evaluate the differences in restructuring-destructuring kinetics of the a-La gels and also the levels of consistency reached as a function of NaCl ionic strength, a procedure identical to that presented in table I was carried out on various suspensions of a-La. The results are given in FIGS. 7 to 9.

Figure 10:
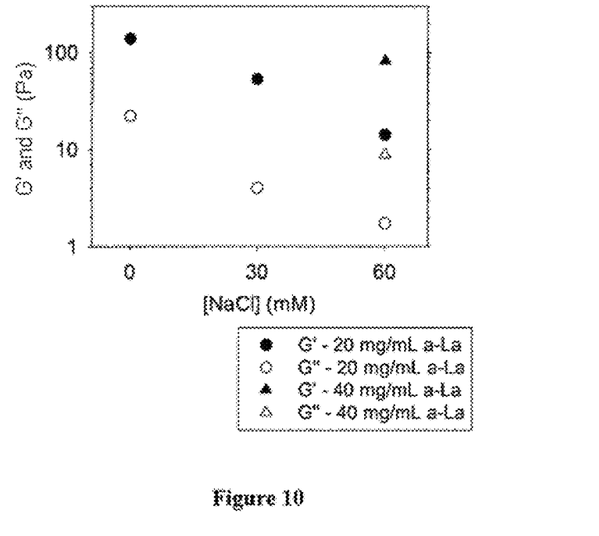
FIG. 10 compares the levels of the viscoelastic moduli G' and G" as a function of the ionic strength of NaCl and of the concentration of a-La: the modulus G' for a hydrogel at 20 mg/ml of a-La is represented by solid disks, the modulus G" for a hydrogel at 20 mg/ml of a-La is represented by open disks, the modulus G' for a hydrogel at 40 mg/ml of a-La is represented by solid triangles and the modulus G' for a hydrogel at 40 mg/ml of a-La is represented by open triangles. The levels were compared at the same 500 s restructuring time of step 3 corresponding to the slow restructuring kinetics zone.

Represented in FIG. 10 is the change in the viscoelastic moduli G' and G" as a function of the NaCl ionic strength and of the a-La concentration. The levels were compared at the same 500 s restructuring time of step 3 corresponding to the slow restructuring kinetics zone, i.e. on the "plateau" reached during the restructuring. It is demonstrated that the levels of G' and G" decrease when the ionic strength increases, which corresponds to a reduction in the consistency of the gel. The increase in the a-La concentration leads to an increase in the viscoelastic moduli.

Figure 11:
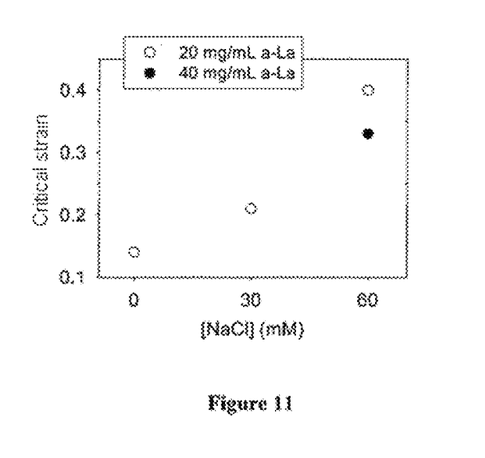
FIG. 11 is a graph which compares the levels of critical strain $\gamma_c$ as a function of the ionic strength of NaCl and of the concentration of a-La (open disks for an a-La concentration of 20 mg/ml and solid disks for an a-La concentration of 40 mg/ml). For each condition, the destructuring phenomenon is very reproducible, which demonstrates the high capacity of the system to undergo various shear stresses without undergoing physicochemical modification or any denaturation.

FIG. 11 shows a comparison of the destructurings applied to various samples; these results demonstrate that the critical strain moves toward higher levels when the ionic strength increases or when the protein concentration decreases. Successive destructurings of one and the same sample exhibit critical strains of the same order of magnitude (not represented in the figure), which demonstrates the very good stability of the system with respect to undergoing successive destructuring-restructuring actions, and also a very good stability over time by virtue of the reproducibility of the G' and G" measurements.

EXAMPLE 4

Preparation of an α-Lactalbumin Hydrogel
According to the Conditions Described in the
Thesis of C. Blanchet The purpose of this test is to reproduce an a-La suspension which can be obtained by means of the protocol described by C. Blanchet et al. and then to characterize its rheological properties.

The experiments were carried out under the conditions and according to the protocol described on page 203 of the thesis: the a-La proteins (10 mg/ml with 30 mM of NaCl) are placed in suspension, the pH of this suspension is then adjusted to 2 and then the suspension is placed in an Eppendorf tube; the tube is stirred at 40° C. (the stirring conditions are those used for preparing the hydrogels according to the invention).

In parallel, a hydrogel containing 10 mg/ml of a-La with 30 mM of NaCl is prepared by means of the process according to the invention.

Figure 13:
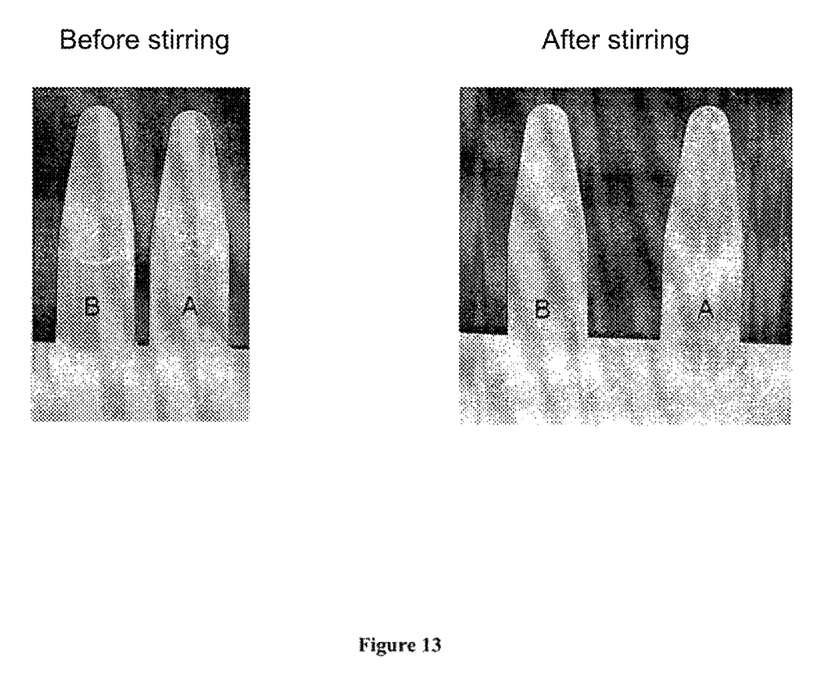
FIG. 13 comprises two images of Eppendorf tubes comprising, on the one hand, a hydrogel prepared according to the protocol of the thesis of C. Blanchet (B) and, secondly, a hydrogel according to the invention (A). The image on the left shows these two hydrogels after they had been prepared (both are in the conical end of the tubes); the image on the right shows these two hydrogels after stirring; the hydrogel (A) according to the invention is in the bottom part of the Eppendorf tube, whereas the hydrogel (B) has remained in the top part (conical end).

The image on the left in FIG. 13 illustrates the appearance of the hydrogels thus obtained ((B) according to the thesis and (A) according to the invention): the hydrogel (B) has a less homogeneous appearance than the hydrogel (A).

It is also observed that these two hydrogels do not have the same behavior when they are stirred: the image on the right in FIG. 13 shows these two hydrogels after stirring. Because of its thixotropic behavior, the viscosity of the hydrogel (A) according to the invention decreased during the stirring and it flowed into the bottom part of the Eppendorf tube; conversely, the stirring did not bring about any flow of the hydrogel (B), which remained in the top part of the Eppendorf tube (conical end).

EXAMPLE 5

Preparation of an α-Lactalbumin Hydrogel at pH 7 and 80° C.

The purpose of this test is to reproduce the hydrogel described by Kavanagh, G. M., A. H. Clark, et al. (2000). "*Heat-induced gelation of beta-lactoglobulin/alpha-lactalbumin blends at pH 3 and pH 7.*" Macromolecules 33(19): 7029-7037, and then to characterize its rheological properties.

Conditions Described in the Article:
 a-La concentration of 15% (w/w), i.e. 150 mg/ml
 T° C.=80° C.
 Solvent=deionized water
 pH=7.0
 The gels are observed after 1 to 2 h at 80° C.

Conditions Implemented:
 a-La concentration of 15% (w/w), i.e. 150 mg/ml
 T° C.=80° C. for 1 h
 Solvent=deionized water
 pH=7.2.

The a-La concentration is verified by measuring the absorbance at 280 nm of the solution using a Nanodrop® ND-1000 spectrophotometer (LabTech): the measurements are carried out on three solutions of proteins each diluted five-fold: A1=61; A2=62; A3=61. The a-La concentration is determined according to the Beer-Lambert law $A=\epsilon C\, l$ where $\epsilon=27\,880$ $L\cdot mol^{-1}\cdot cm^{-1}$ and l=1 cm. The molar concentration C of the a-La solution is therefore 10.9 mM, which corresponds to a concentration by weight of 154 mg/ml (the molar mass of a-La is 14 150 $g\cdot mol^{-1}$).

The a-La solution prepared is separated into two tubes of 200 µl. One tube is placed at 80° C. for 1 h without stirring and the other tube is kept at ambient temperature as a control.

In less than one hour, a hydrogel formed in the tube placed at 80° C. The gel obtained is hard, a tip cannot be pushed into it, but shows a certain elasticity. It is also possible to remove it from the mold while retaining the shape of the tube, which is not the case with the hydrogels according to the invention, which have a softer consistency.

The hydrogel thus obtained also has a more transparent appearance, whereas the hydrogels according to the invention are translucent (they allow a scattered light to pass through, but objects cannot be distinguished through these hydrogels). Finally, if it is vigorously shaken, it does not change shape, it is irreversible.

The hydrogel produced here thus has neither the appearance nor the physical properties of the thixotropic gels prepared according to the process of the invention.

LITERATURE

Akkermans, C., P. Venema, et al. (2006). "Peptides are building blocks of heat-induced fibrillar protein aggregates of beta-lactoglobulin formed at pH 2." *Biomacromolecules* 9(5): 1474-1479.

Audic, J. L., B. Chaufer, et al. (2003). "Non-food applications of milk components end dairy co-products: A review." *Lait* 83(6): 417-438.

Chen, H. (1995). "Functional properties and applications of edible films made of milk proteins." *Journal of Dairy Science* 78(11): 2563.2583.

Gosal, W. S., A. H. Clark, et al. (2004). "Fibrillar bet-lactoglobulin gels: Part 1. Fibril formation and structure." *Biomacromolecules* 5(6): 2408-2419.

Gosal, W. S., A. H. Clark, et al. (2004). "Fibrillar beta-lactoglobulin gels: Part 2. Dynamic mechanical characterization of heat-set systems." *Biomacromolecules* 5(6): 2420-2429.

Gosal, W. S., A. H. Clark, et al. (2004). "Fibrillar beta-lactoglobulin gels: Part 3. Dynamic mechanical of solvent-induced systems." *Biomacromolecules* 5(6): 2430-2438.

Graveland-Bikker, J. F., R. Ipsen, et al. (2004). "Influence of calcium on the self-assembly of partially hydrolyzed alpha-lactalbumin." *Langmuir* 20(16): 6841-6846.

Gunasekaran, S., S. Ko, et al. (2007). "Use of whey proteins for encapsulation and controlled delivery applications." *Journal of Food Engineering* 83(1): 31-40.

Heidebach, T., P. Forst, et al. (2009). "Microencapsulation of probiotic cells by means of rennet-gelation of milk proteins." *FOOD HYDROCOLLOIDS* 23(7): 1670-1677.

Heidebach, T., P. Forst, et al. (2009). "Transglutaminase-induced caseinate gelation for the microencapsulation of probiotic cells." *INTERNATIONAL DAIRY JOURNAL* 19(2): 77-84.

Hines, M. E. and E. A. Foegeding (1993). "INTERACTIONS OF ALPHA-LACTALBUMIN AND BOVINE SERUM-ALBUMIN WITH BETA-LACTOGLOBULIN IN THERMALLY INDUCED GELATION." *Journal of Agricultural and Food Chemistry* 41(3): 341-346.

Holmes, T. C., S. de Lacalle, et al. (2000). "Extensive neurite outgrowth and active synapse formation on self-assembling peptide scaffolds." *Proceedings of the National Academy of Sciences of the United States of America* 97(12): 6728-6733.

Ipsen, R. and J. Otte (2007). "Self-assembly of partially hydrolysed alpha-lactalbumin." *BIOTECHNOLOGY ADVANCES* 25(6): 602-605.

Ipsen, R., J. Otte, et al. (2001). "Molecular self-assembly of partially hydrolysed alpha-lactalbumin resulting in strong gels with a novel microstructure." *Journal of Dairy Research* 68(2): 277-286.

Kamau, S. M., S. C. Cheison, et al. (2010). "Alpha-Lactalbumin: Its Production Technologies and Bioactive Peptides." *Comprehensive Reviews in Food Science and Food Safety* 9(2): 197-212.

Kavanagh, G. M., A. H. Clark, et al. (2000). "Heat-induced gelation of beta-lactoglobulin/alpha-lactalbumin blends at pH 3 and pH 7." *Macromolecules* 33(19): 7029-7037.

Kavanagh, G. M., A. H. Clark, et al. (2000). "Heat-induced gelation of globular proteins: part 3. Molecular studies on low pH beta-lactoglobulin gels." *International Journal of Biological Macromolecules* 28(1): 41-50.

Kopecek, J. and J. Yang (2009). "Peptide-directed self-assembly of hydrogels." *Acta Biomater* 5(3): 805-816.

Kyle, S., A. Aggeli, et al. (2009). "Production of self-assembling biomaterials for tissue engineering." *Trends in Biotechnology* 27(7): 423-433.

Le Tien, C. C. Vachon, et al. (2001). "Milk protein coatings prevent oxidative browning of apples and potatoes," *Journal of Food Science* 66(4): 512-516.

Livney, Y. D. (2010). "Milk proteins as vehicles for bioactives." *Current Opinion in Colloid & Interface Science* 15(1-2): 73-83.

Loveday, S. M., M. A. Rao, et al. (2009). "Factors Affecting Rheological Characteristics of Fibril Gels: The Case of beta-Lactoglobulin and alpha-Lactalbumin." *Journal of Food Science* 74(3): R47-R55.

Madureira, A. R., C. I. Pereira, et al. (2007). "Bovine whey proteins—Overview on their main biological properties" *Food Research International* 40(10): 1197-1211.

Mewis, J. (1979). "THIXOTROPY—GENERAL-REVIEW." *Journal of Non-Newtonian fluid Mechanics* 6(1): 1-20.

Oboroceanu, D., L. Wang, et al. (2010). "Characterization of β-Lactoglobulin Fibrillar Assembly Using Atomic Force Microscopy, Polyacrylamide Gel Electrophoresis, and in Situ Fourier Transform Infrared Spectroscopy." *Journal of Agricultural and Food Chemistry*.

Paulsson, M., P. O. Hegg, et al. (1986). "HEAT-INDUCED GELATION OF INDIVIDUAL WHEY PROTEINS A DYNAMIC RHEOLOGICAL STUDY." *Journal of Food Science* 51(1): 87-90.

Pek, Y. S., A. C. A. Wan, et al. (2008). "A thixotropic nanocomposite gel for three-dimensional cell culture." *Nature Nanotechnology* 3(11): 671-675.

Permyakov, E. A. and L. J. Berliner (2000). "alpha-Lactalbumin: structure and function." *Febs Letters* 473(3): 269-274.

Piau, J. M. (2007). "Carbopol gels: Elastoviscoplastic and slippery glasses made of individual swollen sponges Meso- and macroscopic properties, constitutive equations and scaling laws." *Journal of Non-Newtonian Fluid Mechanics* 144(1): 1-29.

Pignon, F., A. Magnin, et al. (1998). "Thixotropic behavior of day dispersions: Combinations of scattering and rheometric techniques." *Journal of Rheology* 42(6): 1349-1373.

Restani, P., C. Ballabio, et al. (2009). "Molecular aspects of milk allergens and their role in clinical events." *ANALYTICAL AND BIOANALYTICAL CHEMISTRY* 395(1): 47-56.

Rodrigues, M. M. A., A. R. Simioni, et al. (2009). "Preparation, characterization and in vitro cytotoxicity of BSA-based nanospheres containing nanosized magnetic particles and/or photosensitizer." *Journal of Magnetism and Magnetic Materials* 321(10): 1600-1603.

Semo, E., E. Kasselman, et al. (2007). "Casein micelle as a natural nano-capsular vehicle for nutraceuticals." *Food Hydrocolloids* 21(5-6): 936-942.

Song, F., L. Zhang, et al. (2009). "Genipin-crosslinked casein hydrogels for controlled drug delivery." *INTERNATIONAL JOURNAL OF PHARMACEUTICS* 373(1-2): 41-47.

Tokpavi, D. L., P. Jay, et al. (2009). "Experimental study of the very slow flow of a yield stress fluid around a circular cylinder." *Journal of Non-Newtonian Fluid Mechanics* 164(1-3): 35-44.

van der Linden, E. and P. Venema (2007). "Self-assembly and aggregation of proteins." *Current Opinion in Colloid & Interface Science* 12(4-5): 158-165.

Vintiloiu, A. and J.-C. Leroux (2008). "Organogels and their use in drug delivery—A review." *JOURNAL OF CONTROLLED RELEASE* 125(3): 179-192.

Yan, H., H. Frielinghaus, et al. (2008). "Thermoreversible lysozyme hydrogels: properties and an insight into the gelation pathway." *Soft Matter* 4(6): 1313-1325.

Yan, H., A. Saiani, et al. (2006). "Thermoreversible Protein Hydrogel as Cell Scaffold." *Biomacomolecues* 7(10): 2776-2782.

Yantian, Y., K. Ulung, et at. (2009). "Designer self-assembling peptide nanomaterials." *Nano Today* 4(2): 193-210.

Zhang, S. (2008). Designer self-assembling peptide nanofiber scaffolds for study of 3-0 cell biology and beyond. *Advances in Cancer Research*. Vol 99. San Diego, Elsevier Academic Press Inc. 99: 335-+.

The invention claimed is:

1. process of preparing an α-lactalbumin hydrogel from an aqueous suspension of α-lactalbumin at a concentration $C_{a-La}$ of between 5 and 60 mg/ml, comprising the following steps:
   (a) suspending the α-lactalbumin in an acidic aqueous solution having an ionic strength of an added salt of less than or equal to 60 mM; said suspending consisting in:
      (a1) preparing an acidic aqueous solution having a concentration of protons expressed in mM determined by the sum: (numerical value of $C_{a-La}$ expressed in g/l) +10;
      (a2) suspending the α-lactalbumin in said acidic aqueous solution; and
      (a3) adjusting the pH to a value of between 1.5 and 2.5;
   (b) forming the gel from said α-lactalbumin suspension obtained at the end of step a); said forming of the gel is carried out under the following conditions;
      at a temperature below 60° C.;
      with stirring having a strength defined by a Reynolds number of between 37 and 1000;
      for 10 hours to 1 week, and
      in the absence of evaporation of water from said α-lactalbumin suspension,
   wherein said α lactalbumin hydrogel is an α lactalbumin shear-thinning hydrogel which has a yield point and is thixotropic, having an α lactalbumin content of between 5 and 60 mg/ml, a pH of between 1.5 and 2.5 and an ionic strength of an added salt of less than or equal to 60 mM.

2. The process according to claim 1, wherein the Reynolds number is between 300 and 500.

3. The process according to claim 1, wherein the temperature is between 35 and 55° C.

4. The process according to claim 1, wherein the pH is between 1.8 and 2.2.

5. The process according to claim 1, wherein the α-lactalbumin suspension obtained at the end of step (a) is filtered.

6. An α-lactalbumin shear-thinning hydrogel obtained according to the process of claim 1.

7. An α-lactalbumin shear-thinning hydrogel which has a yield point and is thixotropic, having an α-lactalbumin content of between 5 and 60 mg/ml, a pH of between 1.5 and 2.5and an ionic strength of less than or equal to 60 mM.

8. A food product comprising at least one α-lactalbumin shear-thinning hydrogel of claim 6.

9. A dressing comprising at least one α-lactalbumin shear-thinning hydrogel of claim 6, and optionally at least one active compound, such as a healing agent or an antimicrobial agent.

10. A cosmetic composition comprising at least one α-lactalbumin shear-thinning hydrogel of claim 6.

11. A paint comprising at least one α-lactalbumin shear-thinning hydrogel of claim 6.

12. A method of treating a wound in a subject in need thereof comprising administering to the wound the dressing according to claim 9.

13. An α-lactalbumin shear-thinning hydrogel which has a yield point and is thixotropic, having an α-lactalbumin content of between 5 and 60 mg/ml and an ionic strength of an added salt of less than or equal to 60 mM.

14. A method of enhancing texture of a food product comprising adding the αlactalbumin shear-thinning hydrogel produced by the process of claim 1 to the food product.

15. A method of preparing a cosmetic comprising adding the α-lactalbumin shear-thinning hydrogel produced by the process of claim 1 to the cosmetic.

16. A method of preparing paint comprising adding the α-lactalbumin shear-thinning hydrogel produced by the process of claim 1 to the paint.

\* \* \* \* \*